United States Patent [19]
Deetz et al.

[11] Patent Number: 5,223,433
[45] Date of Patent: Jun. 29, 1993

[54] TEMPERATURE STABILIZED FLUID CALIBRATION SYSTEM

[75] Inventors: David W. Deetz, North Oaks; Russell L. Morris, St. Paul, both of Minn.

[73] Assignee: Diametrics Medical Inc., Roseville, Minn.

[21] Appl. No.: 806,495

[22] Filed: Dec. 13, 1991

[51] Int. Cl.⁵ .......................................... G01N 31/00
[52] U.S. Cl. ........................................ 436/8; 436/11; 436/16; 436/68
[58] Field of Search ................. 422/62, 83; 436/8, 11, 436/9, 16, 55, 68

[56] References Cited

U.S. PATENT DOCUMENTS

| | | |
|---|---|---|
| 4,001,142 | 1/1977 | Turner ................... 436/11 |
| 4,116,336 | 9/1978 | Sorenson et al. ........ 436/11 |
| 4,126,575 | 11/1978 | Louderback ............ 436/11 |
| 4,151,108 | 4/1979 | Sorenson et al. ........ 436/11 |
| 4,163,734 | 8/1979 | Sorenson et al. ........ 436/11 |
| 4,279,775 | 7/1981 | Louderback et al. .... 436/11 |
| 4,299,728 | 11/1981 | Cormier et al. ......... 436/11 |
| 4,369,127 | 1/1983 | Cormier et al. ......... 436/11 |
| 4,469,792 | 9/1984 | Simmonds et al. ...... 436/16 |
| 4,485,174 | 11/1984 | Chiang et al. .......... 436/11 |
| 4,722,904 | 2/1988 | Feil ......................... 436/11 |
| 4,851,195 | 7/1989 | Matthews et al. ....... 436/68 |
| 4,960,708 | 10/1990 | Zowtiak et al. ......... 436/11 |

OTHER PUBLICATIONS

Merck Index, 10th Edition, Windholz et al. (eds), p. 3742 (1983).

Primary Examiner—James C. Housel
Assistant Examiner—Lien Tran
Attorney, Agent, or Firm—Haugen and Nikolai

[57] ABSTRACT

A method and system for controlling the concentration of one or more gaseous species of interest in a sample medium throughout a range of temperatures in which a temperature related, time variable dominant independent source of the gaseous species of interest is used to control the partial pressure of one or more gaseous species of interest contained in the sample medium in a manner such that the concentration of the gaseous species of interest in the sample medium remains essentially the same over the temperature range. The source of the gaseous species of interest comprises a reservoir containing an amount of a temperature sensitive source of the gaseous species of interest. The sample and the reservoir are contained in separate fluid-tight, gas-permeable enclosures further confined by a common substantially gas-tight enclosure.

30 Claims, 3 Drawing Sheets

TEMPERATURE STABILIZED FLUID CALIBRATION SYSTEM

BACKGROUND OF THE INVENTION

I. Field of the Invention

The present invention is directed generally to a packaged, temperature stabilized reference or calibration system and, more particularly, to a method and system for stabilizing the concentration of a dissolved gaseous species of interest in a calibration sample medium by the provision of a reversible compensating reservoir or independent temperature dependent source of the dissolved species of interest which compensates the temperature dependency in the sample medium over the useful temperature range of the system.

II. Description of the Related Art

The field of diagnostic medicine is fast becoming more sophisticated and complex. The ability to make rapid or immediate diagnostic determinations characteristic of the current condition of a patient so that the proper emergency steps may be taken in a timely manner to improve or stabilize the condition of the patient, for example, during surgery or during the treatment of traumatic injury has become very important. The partial pressures of oxygen ($PO_2$) and carbon dioxide ($PCO_2$) in the blood are examples of extremely important instantaneous indications of respiratory deficiency, efficiency of inhalation therapy, renal function and other vital bodily processes. These measurements are made utilizing stationary clinical laboratory instruments which measure the parameters at a specific temperature and which are periodically calibrated to operate by a calibration system which is accurate only at a specific temperature. Calibration and use of the instruments are thus keyed to opening the calibration fluid, calibrating the instrument, and operating the instrument at a specific known temperature, e.g., 37° C. The specific composition of typical control or calibration fluid systems is such that the reference or known equilibrium partial pressures of oxygen and carbon dioxide are temperature dependent and so occur only at the specific calibration temperature, and opening or using the calibration system at a temperature other than the designed temperature may introduce a decided amount of error into the readings. Alternatively, gaseous $CO_2$ and $O_2$ can be used to calibrate the instrument, but that requires the need for compressed gas cylinders for storage of the gases.

A definite need exists for a calibration system which is small, easily portable and less temperature dependent to thereby enable the calibration of such devices as diagnostic systems of the class described to be accurately accomplished over a reasonable range of ambient temperatures. This, of course, applies to the temperature stabilization of the amount of contained dissolved or dissociated gaseous species of interest in a variety of media for a variety of applications. In this regard, particularly with respect to oxygen, one approach that has been used involves the use of relatively inert fluids which have the ability to dissolve rather large amounts of oxygen and which are stable with respect to biological media. One class of such compounds consists of fluorinated organic compounds known as perfluorocarbons. Certain other systems or approaches have been proposed to stabilize and buffer the partial pressure of species such as carbon dioxide, normally in an aqueous phase, which, when combined, may be emulsified with the perfluorocarbon phase.

In a co-pending application Ser. No. 07/604,666, filed Oct. 26, 1990, now abandoned, and assigned to the same assignee as the present invention, one approach is disclosed in which a perfluorocarbon-based system is used which contains sufficient perfluorocarbon to give it ability to remain stable with respect to the relative concentration of dissolved oxygen over a range of ambient temperatures for example, between about 20° C. and 30° C. An aqueous solution phase, which contains a specific amount of one or more $CO_2$ complexing agents, such as ethylene diamine, $HCO_3^-$, $Ca++$ and $OH^-$, or the like, as agents to buffer the partial pressure of carbon dioxide in the aqueous phase is used to reduce sensitivity to changes in temperature with respect to complexed $CO_2$. To the extent any information is deemed necessary to the proper completion or explanation with regard to material contained in the present application, such may be deemed incorporated by reference herein.

The present invention involves a simple and accurate method for reversibly controlling the partial pressure of a contained dissolved or dissociated gaseous species of interest in a medium which exhibits time/temperature stability that would be applicable to a species such as carbon dioxide. Thus, for example, the design of a prepackaged calibration system which is usable to quickly and accurately calibrate an instrument over a range of ambient temperatures is now possible.

SUMMARY OF THE INVENTION

In accordance with the present invention, it has been found possible to create a packaged system that can be used to provide a stable concentration of a gas in a sample medium despite changes in the temperature of the sample within a reasonable range of ambient temperature. The system involves the use of an additional separate reversible equilibrium compensating source containing an amount of the gas or gases of interest. The additional source or "reservoir" provides the ability to control changes in the partial pressure of the gas or gases of interest in the atmosphere of the package including the atmosphere contacting the sample liquid. The changes in partial pressure can be tailored to exactly compensate for changes in the solubility of the gas or gases of interest in the calibration sample over a designed range. The system can also be used to control change in the partial pressure of a species of interest as a function of temperature change.

Both the sample medium enclosure and the reservoir are contained in liquid-tight, gas-permeable enclosures within an outer, common enclosure such that gaseous species may be exchanged with respect to the common atmosphere of the sealed outer enclosure. The reservoir equilibrium is designed to be more temperature dependent and its enclosure more permeable for the gas(es) of interest than the sample and, therefore, to react more quickly to temperature changes and thus to dominate changes produced in the sample container. Temperature changes which produce an increase or decrease in the partial pressure of a species of interest in the reservoir medium will cause a corresponding increase or decrease in the partial pressure of that species in the common atmosphere. This, in turn, anticipates and compensates changes that otherwise would occur thereafter in the sample.

In operation, using the general case as an example, as the temperature of the environment and thus of the entire package including the sample and reservoir rises, the solubility of the gaseous species of interest in the sample decreases. This also occurs in the reservoir. To keep the concentration of the gas or gases of interest from changing in the sample, the reservoir expels amounts of the gas or gases into the package atmosphere anticipating the reaction of the sample by raising the partial pressures of these gases in the common atmosphere and thereby preempting the thermodynamic driving force for the gases to leave through the permeable shell of the sample container. In other words, the gas or gases of interest are preferably released and permeate the shell of the reservoir and increase the partial pressure of these species in the package atmosphere at a somewhat faster rate than they are lost from the sample medium such that the thermodynamic driving force for the gases to leave the sample and diffuse through the wall of the sample enclosure is eliminated. Conversely, if the system cools and the solubility of the gases of interest in the sample medium increases, the reservoir acts to reverse the phenomena of the heating mode and be reabsorbed into the reservoir medium from the package atmosphere at a somewhat faster rate than the reabsorption in the sample medium thereby lowering the partial pressure of the gas or gases of interest in the common atmosphere to eliminate any driving force for the gas or gases of interest in the common atmosphere to permeate the sample enclosure and dissolve in the sample medium. This preserves the resulting concentration of each such species of interest in the sample medium regardless of the direction of temperature change within a designed limited ambient temperature range.

Typically, the sample medium and/or the reservoir medium are solutions of selective solvents with or without complexing agents or buffers. In the case where $CO_2$ is the species of interest, both the reservoir and the sample media may be aqueous solutions of $CO_2$. A system where the sample pH is 7.4 and the reservoir is buffered to a pH of 8.6, for example, exhibits good temperature/concentration or ($pCO_2$) stability in the 20° C. to 30° C. range; but ($pCO_2$) is quite temperature dependent for a reservoir pH above 9.0. The invention, however, is not limited to the use of solutions as media. Gels or even solids exhibiting the properties required with respect to taking on and giving up the gaseous species can be employed. Gels may be based on natural materials such as collagen or agarose or based on synthetic materials such as polymers of a desired average molecular weight. Solids may include higher average molecular weight polymers or other materials which reversibly accept the species of interest. Of course, the sample medium may differ from or be the same type of medium as that of the reservoir. The material may undergo a phase change such as liquification at a temperature just above ambient.

In a preferred embodiment, the typical environment of the invention is a sealed package, which might be a flexible poly-foil pouch, gas-filled, but not pressurized above atmospheric pressure, provided in which the sample or calibration medium is contained in a separate enclosure within the pouch such as a sealed, gas-permeable polymeric container. An additional liquid-tight, gas-permeable enclosure is provided in the form of the reservoir containing the reversibly available additional amount or amounts of the gas or gases of interest.

BRIEF DESCRIPTION OF THE DRAWINGS

In the drawings, wherein like numerals are utilized to designate like partes throughout the same.

DETAILED DESCRIPTION

It will be appreciated that the concepts of the present invention can be modeled from thermodynamic principles for gaseous species and solutions of known reversible solubilities and permeabilities. As an example, the preferred or illustrative embodiment of this detailed description contemplates a system in which the gas carbon dioxide ($CO_2$) is the dissolved or complexed calibration species of interest, the concentration of which is sought to be controlled. The $CO_2$ is normally contained in a buffered aqueous solution which, for blood gas calibration or control, is used together with an amount of a perfluorocarbon-based medium containing oxygen, sealed in a rather slender sample tube in which the two phases are in intimate contact but do not mix. The sample tube, which may be Tygon ® (trademark of United States Stoneware Company) is further contained in a poly-foil substantially gas-tight, flexible pouch. The pouch is one which describes a flexible package which may be layered polyethylene with an aluminum foil layer or layers to provide a substantially gas-tight system with an internal pressure about equal to the external atmospheric pressure but not inflated above it, as is the case with a balloon. Of course, the system could also be designed using a rigid wall container such as a glass ampule as the package.

The aqueous sample is typically 500 micro-liters of an aqueous phosphate buffer at pH 7.4. A larger, possibly 5 ml, bicarbonate and carbonate containing aqueous solution in the pH range of 8.0 to 9.0 is also in the package in a separate liquid-tight gas-permeable sealed bag made of polyethylene or other gas-permeable material to serve as the reservoir. The reservoir solution may also contain a buffer salt to give it a more temperature dependent pH. As the temperature of the system of this embodiment increases, the pH of the reservoir decreases, and this, in combination with the decrease in the solubility of $CO_2$ in the warmer medium, shifts the equilibrium of the $CO_2$ system consisting of the reservoir and the common or package environment toward a higher partial pressure of $CO_2$ in the package atmosphere. The increase in package partial pressure prevents the sample from losing $CO_2$ to the gas phase of the package environment through the Tygon tube. Conversely, if the temperature of the package is decreased, the pH of the reservoir and the solubility of $CO_2$ in the reservoir will increase at a greater rate than that in the sample. This will lead to a lower partial pressure of $CO_2$ in the common atmosphere or gas phase of package in relation to that of equilibrium in the sample such that $CO_2$ will not have a tendency to migrate from the package into the sample. Thus, regardless of the direction of the temperature change, the resulting concentration of $CO_2$ in the sample will not change with changing temperature over the selected range.

In an alternate embodiment, the temperature dependence of the solubility of $CO_2$ in the reservoir medium can be utilized without the additional effect of the temperature dependence of the pH of the reservoir solution. It is necessary, however, that the capacity of the reservoir for the gas be greater than that of the sample to insure that the reservoir will lead and dominate the gas phase of the package throughout the temperature range of interest. Whatever the thermodynamic temperature dependent property or properties selected as the criteria for the reservoir is, the basic kinetic requirement for the system remains that the reservoir needs to respond somewhat faster to the changes in temperature than the sample environment. This can be based on relative volumes, composition, relatively solubilities of the gas or gases of interest in the reservoir and in the sample, pH control, or even the utilization of different permeabilities with respect to the sample and reservoir enclosures such that the gas or gases of interest diffuse in and out of the reservoir enclosure at a higher rate than they do with respect to the sample container. It will further be appreciated that separate internal containers may be provided for each calibration species if desired or that all of them may be contained in a single solution or emulsion to address a particular application of the concept.

Systems formulated in accordance with the teachings of the present invention can be formulated to exhibit stable overall concentrations with respect to the gases of interest within a range of ambient temperatures, such as between about 20° C. and 30° C. In practical terms, this means, for example, that a sample calibration system can be opened and exposed to the ambient environment at any temperature within that range and used within a reasonable time without fear of calibration inaccuracy. Thus, in accordance with the present invention, the equilibrium solubility of any volatile constituent of a solution at a given temperature can be artificially controlled by compensating for anticipated changes in the partial pressure of that constituent in the vapor phase above the solvent medium in relation to the effects of temperature. The invention provides a means of offsetting the extreme temperature sensitivity of critical concentrations of dissolved gaseous species in liquids, gels or solids.

In accordance with the illustrative embodiment, the dissolved species of interest is exemplified by carbon dioxide ($CO_2$) and its relation to temperature and pH in an aqueous solution. It is contemplated, however, that such principles can be extended by those skilled in the art to produce similar results with respect to many other gaseous species of interest in the same and other types of solutions.

Figure 4:
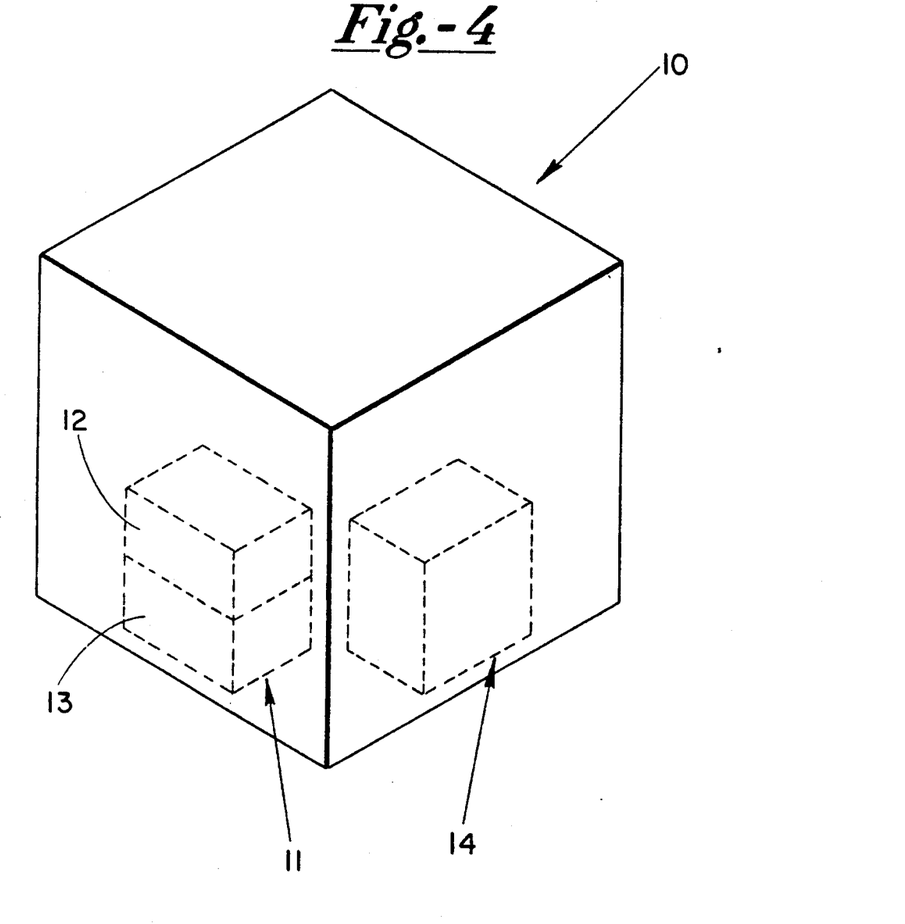
FIG. 4 is a schematic representation of a possible system construction.

One environment of the system is shown generally in FIG. 4 and includes an outer enclosure or package designated by 10 which may be a flexible pouch-type package of poly-foil which has an internal pressure about equal to atmospheric pressure and which is generally impervious to the passage of gases, especially atmospheric molecules including nitrogen, oxygen and carbon dioxide. The package 10 contains a further enclosed sample reservoir, shown generally at 11, which, in turn, contains separate liquid calibration solutions or phases 12 and 13 in intimate contact but not emulsified or mixed. In this respect, phase 12 may contain oxygen reversibly dissolved in a perfluorocarbon substance operating as a source of $O_2$ in the calibration system. Typically, for blood gas analysis, for example, the $pO_2$ is in the range of 10 to approximately 200 mm Hg. The phase 12, then, is an amount of $CO_2$ in reversible equilibrium with water which may contain certain additives, and typically contains a phosphate buffer which establishes the solution at about pH 7.4. The preferred range of partial pressures for $CO_2$ ($pCO_2$) is from about 5 to about 100 mm Hg. The volumes for the calibration solutions are typically 500 micro-liters ($\mu l$). The envelope or ampule 10 further contains an additional separate enclosure in the form of a polyethylene reservoir, or the like, 14. The reservoir is typically much larger volume, e.g., 5 milliliters (ml) v. 500 $\mu l$ of a bicarbonate and carbonate containing aqueous solution buffered in the pH range of about 8.0 to 9.0. It serves as a comparatively large reservoir of carbon dioxide. The reservoir solution may also contain a buffer salt which produces a temperature dependent pH in the reservoir.

The reservoir container enclosure 14 should have a higher permeability for the $CO_2$ or other gaseous species of interest than the sample envelope 11 so that the relative partial pressure of the species of interest in the envelope 10 outside of both internal containers is dominated both in terms of size and time by the reaction of the material in the reservoir 14 rather than that in the sample tube 11. As recited above, the general thermodynamic design of the compensating system is such that as the temperature of the package and the aqueous sample solution 13 increases and the solubility of the $CO_2$ in the sample decreases; the reservoir 14 expels $CO_2$ gas into the package atmosphere raising the partial pressure of the $CO_2$ in the package atmosphere and thereby eliminating the compositional thermodynamic driving force for $CO_2$ to leave the sample enclosure 13. Conversely, when the system is cooled, the reservoir reverses its action and receives $CO_2$ gas from the package atmosphere thereby lowering the partial pressure of the $CO_2$ in the package and eliminating any driving force for $CO_2$ in the package atmosphere to dissolve in the sample.

Figure 1:
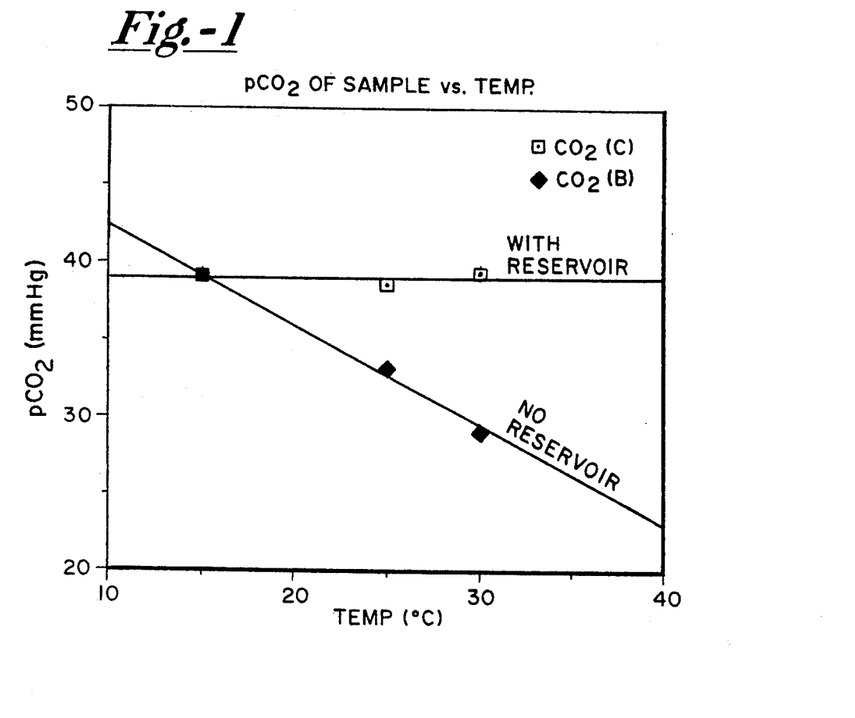
FIG. 1 is a graphical representation of the partial pressure of carbon dioxide ($pCO_2$) of the sample medium, measured at 37° C. vs. the temperature of the sample when it was removed from the package, for a system with and without a compensating reservoir.
Figure 2:
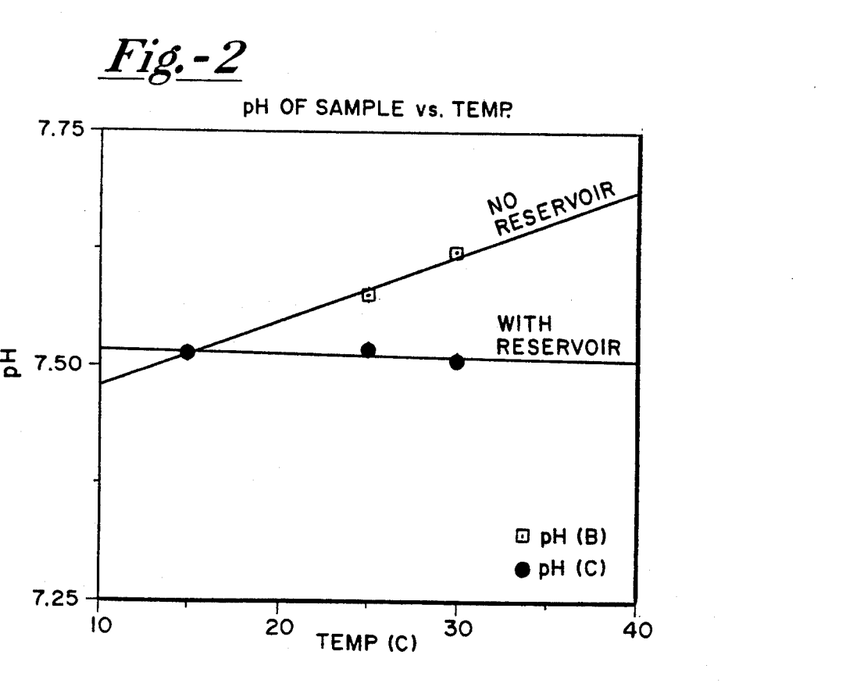
FIG. 2 is a graphical representation of the pH of the sample medium measured at 37° C. vs. the temperature of the sample when it was removed from the package, for a similar system to that of FIG. 1 with and without a compensating reservoir.

So long as the operation of the reservoir system dominates the atmosphere of the package, both in terms of size and time, the system functions very well. This is depicted in FIG. 1 where it shows an almost constant $pCO_2$ for data points in the range of about 15° C. to 30° C. utilizing the reservoir and illustrates the sharp contrast or radical change in $pCO_2$ without the reservoir. Likewise, FIG. 2 illustrates the same principle with respect to pH over the same temperature range. Without the reservoir, the pH is seen to increase with the loss of $CO_2$ from the solution as the temperature is raised from 15° C. to 30° C.

Figure 3:
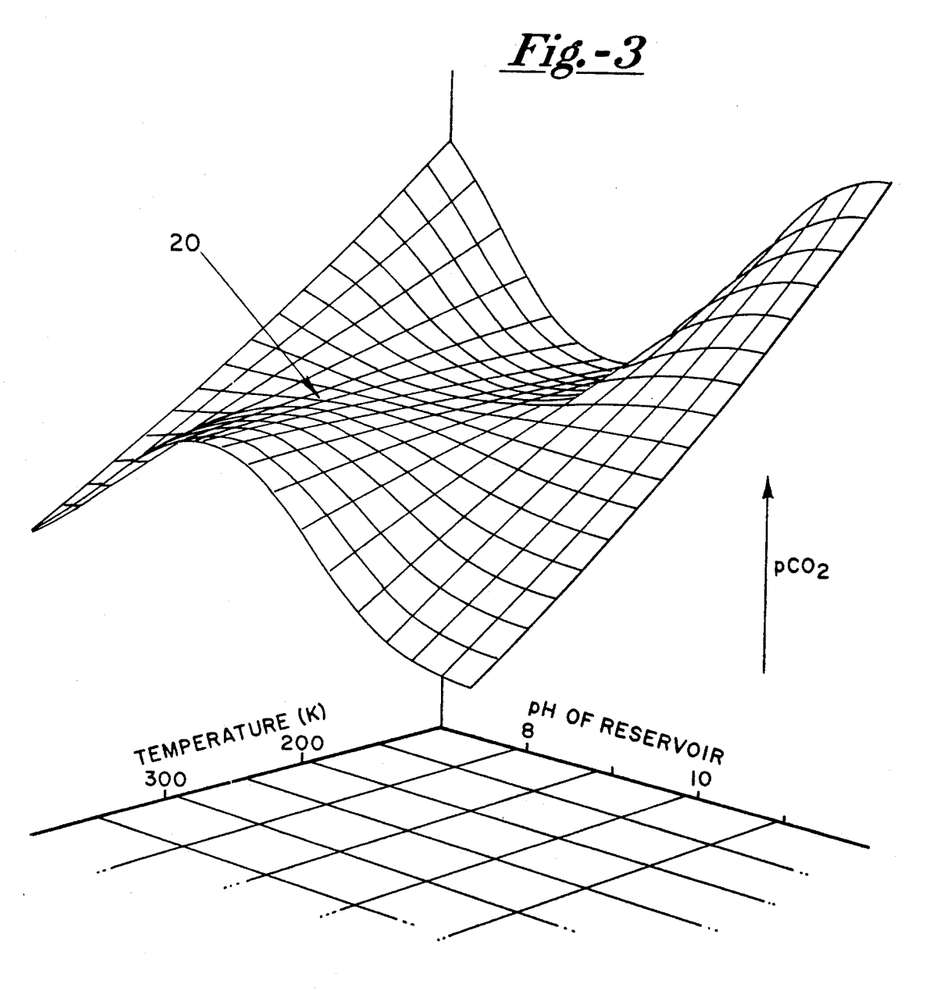
FIG. 3 represents a theoretical response surface based on thermodynamic properties of the species of interest $CO_2$ in which the $pCO_2$ of the sample medium analyzed at 37° C. is plotted with respect to the temperature of the sample at which it was removed from the package and one of the variables associated with the reservoir in the package, namely, the reservoir pH.

Concepts of the present invention further represented as a mathematical model for a $CO_2$ system from known thermodynamic data are shown in the form of the complex surface generated in FIG. 3. That Figure represents a system with 500 micro-liters of buffered aqueous as the calibration sample and 5 ml of reservoir at a higher pH (approximately 8.5 vs. 7.4). The other two axes represent the temperature at which the package was theoretically opened and the $pCO_2$ of the sample when analyzed at 37° C. The plot suggests that the pH of the reservoir significantly affects the $pCO_2$ of the sample at the analysis temperature. A pH in the 8.5 range in the reservoir appears to eliminate the temperature dependence of the $pCO_2$ in the sample, while it is clear that systems with reservoir pHs of 7 or 10, for example, obviously show temperature dependent $pCO_2$ values.

It is now possible to design a system, for example, that as the temperature of the system increases, the pH of the reservoir decreases and this, in combination with a decrease in the solubility of $CO_2$ in the reservoir shifts the equilibrium of the $CO_2$ system consisting of the reservoir and the package environment toward a much higher partial pressure $CO_2$ in the package. This increase in partial pressure prevents the sample from losing $CO_2$ to the gas phase. If the temperature of the package is thereafter decreased, the pH of the reservoir and the solubility of $CO_2$ in the reservoir increase, lowering the partial pressure of $CO_2$ in the common gas phase. Regardless of the direction of temperature change, then, the resulting concentration of $CO_2$ in the sample does not change with changing temperature.

If the reservoir does not dominate the sample in terms of time rate of change, the concentration of $CO_2$ in the sample may not be at its equilibrium value shortly after a temperature change. It will return to the desired level only after the entire system including the gas phase, the sample and the reservoir have reestablished equilibrium at the new temperature.

A successful system can also be designed which makes use of the temperature dependence on the solubility of $CO_2$ in the reservoir only and in which the pH of the reservoir need not be temperature dependent. The principles can also be adapted for use in systems having a plurality of dissolved gases, the partial pressure of one or more of which are sought to be controlled. This may include a plurality of samples and a plurality of compensating reservoirs in a single envelope. Of course, concentration, additives and buffers can be designed and tailored specifically to one's needs in such a situation. Additional parameters which may be varied in accordance with the principles of the invention include the volume of the gas phase in the envelope, the relative volume and composition of the reservoir, solubility of gas in the reservoir, composition of the sample, and the solubility of gas in the sample.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself.

What is claimed is:

1. A method of controlling a concentration of a gaseous species of interest in a reference medium as a predetermined function of temperature throughout a selected temperature range comprising steps of:

separating the reference medium containing the gaseous species of interest in a gas-permeable reference enclosure;

providing a separate source of greater sensitivity to temperature change over a selected range of the gaseous species of interest comprising a gas permeable reservoir for the gaseous species of interest outside but in communication with the gas permeable reference enclosure, the reservoir comprising a reservoir medium containing the gaseous species of interest that provides a temperature sensitive source of amounts of the gaseous species of interest;

enclosing said reference medium and said source in a substantially gas-tight hollow structure in the form of a common enclosure for containing both the reference enclosure and the reservoir enclosure surrounded by a gas phase that forms a common atmosphere; and compensating for temperature fluctuations within said selected temperature range in the structure by variance of a partial pressure of the gaseous species of interest in the reservoir as a function of temperature change such that the concentration of the gaseous species of interest in the reference medium remain substantially constant over the selected temperature range.

2. The method of claim 1 wherein the reservoir is formulated to vary the partial pressure of the gaseous species of interest in a manner which preempts changes in partial pressure of the gaseous species of interest within the reference enclosure to sufficiently keep the concentration of the species of interest in the reference medium within the reference enclosure substantially constant over the selected temperature range.

3. The method of claim 1 wherein at least one of the reservoir and the gas-permeable reference enclosure includes a gas phase.

4. A method of controlling a concentration of the gaseous species of interest in a reference medium essentially as a predetermined function of time variable temperature to maintain a substantially constant contraction throughout a selected temperature range comprising steps of:

separating the reference medium containing an amount of the gaseous species of interest by a gas-permeable reference enclosure, providing a separate source of greater sensitivity to temperature change over the selected range of the gaseous species of interest comprising a reservoir enclosure having a reservoir medium containing an amount of the gaseous species of interest in gas-permeable relation to the reference enclosure;

enclosing said reference medium and said source in a substantially gas-tight hollow structure in the form of a common enclosure for containing both the reference enclosure and the reservoir enclosure surrounded by a gas phase that forms a common atmosphere;

compensating for temperature fluctuations within said selected temperature range in a manner such that changes in temperature produce an exchange of amounts of the species of interest to and from the common atmosphere thereby changing the concentration of the species of interest in the common atmosphere contacting the gas-permeable reference enclosure in a manner that controls change sin equilibrium concentration of the gaseous species of interest within the reference medium and such that the partial pressure of the gaseous species of interest in the common atmosphere contacting the gas-permeable reference enclosure changes as a function of temperature, the concentration of the gaseous species of interest in the reference medium remaining essentially controlled over the changes in temperature over the selected range of temperatures.

5. The method of claim 4 wherein the greater temperature sensitivity of the source is based on the existence of one or more conditions selected from the group consisting of a higher permeability of the reservoir enclosure to the gaseous species of interest than the reference enclosure more rapid changes in the solubility of the species of interest int he reservoir medium with respect to given changes in temperature than the reference medium, higher rate of change in the solubility of the species of interest in the reservoir medium in relation to given changes in temperature than the reference medium and reservoir medium volume being larger than that of the reference medium.

6. The method of claim 5 wherein the partial pressure of the species of interest changes more quickly in the reservoir enclosure than in the sample enclosure in response to a temperature change in the selected temperature range.

7. The method of claim 5 wherein the reservoir has a higher permeability to the gaseous species of interest than the reference enclosure.

8. The method of claim 5 wherein the solubility of the species of interest in the reservoir medium has a higher rate of change in relation to a given change in temperature than that of the species of interest in the reference medium in a temperature range.

9. The method of claim 4 wherein the reference medium and the reservoir medium are selected from the group consisting of liquids, gels and solids, with or without buffers or complexing agents.

10. The method of claim 9 wherein the reference medium is a gel.

11. The method of claim 4 wherein the reference medium and the reservoir medium contain liquid solvents for the species of interest.

12. The method of claim 4 further comprising the step of controlling the concentration of a plurality of gaseous species of interest.

13. The method of claim 4 wherein the gas-permeable reference enclosure means comprises, a gelled solvent for the gaseous species of interest.

14. The method of claim 4 wherein the gas-permeable reservoir means comprises, a gelled solvent for the gaseous species of interest.

15. The method of claim 4 wherein at least one of the reservoir and the gas-permeable reference enclosure includes a gas phase.

16. The method of claim 4 wherein the concentration of the gaseous species in the reference medium is held essentially constant over the selected range of temperature.

17. A method of maintaining the concentration of a gaseous species of interest in a reference medium confined in a gas-permeable reference enclosure substantially constant in a given time variable temperature range comprising steps of:
confining the reference medium containing the gaseous species of interest in a gas-permeable reference enclosure including a gas phase;
providing a separate source of greater sensitivity to temperature over a selected range of the gaseous species of interest comprising a reservoir having a reservoir medium confined in a gas-permeable reservoir including containing an amount of the gaseous species of interest including a gas phase;
enclosing said reference medium and said source in a substantially gas-tight hollow structure in the form of a common enclosure for containing both the reference enclosure and the reservoir enclosure surrounded by a common atmosphere;
compensating for temperature fluctuations within a selected temperature range of the contents in the reservoir in a manner such that changes in temperature related equilibrium causes changes in the partial pressure of the species of interest in the reservoir enclosure which in turn cause exchange of amounts of the species of interest across the gas-permeable reservoir enclosure to and form the common atmosphere thereby changing concentration of the species of interest in the common atmosphere contacting the outer surface of the gas-permeable sample enclosure in a manner that controls changes in equilibrium concentration of the gaseous species of interest within the reference medium so that the partial pressure of the gaseous species of interest in the common atmosphere contacting the outer surface of the gas-permeable reference enclosure changes as a function of temperature, the concentration of the gaseous species of interest in the reference medium remaining essentially constant.

18. The method of claim 17 wherein the greater temperature sensitivity of the source is based on the existence of one or more conditions selected from the group consisting of a higher permeability of the reservoir enclosure to the gaseous species of interest than the reference enclosure more rapid changes in the solubility of the species of interest in the reservoir medium with respect to given changes in temperature than the reference medium, higher rate of change in the solubility of the species of interest in the reservoir medium in relation to given changes in temperature than the reference medium, and reservoir medium volume being larger than that of the reference medium.

19. The method of claim 18 wherein the reservoir enclosure has a higher permeability to the gaseous species of interest than the reference enclosure.

20. The method of claim 18 wherein the solubility of the species of interest in the reservoir enclosure has a higher rate of change in relation to a given change in temperature than that of the species of interest in the reference enclosure in a temperature range.

21. The method of claim 18 wherein the partial pressure of the species of interest changes more quickly in the reservoir enclosure than in the sample enclosure in response to a temperature change in the selected temperature range.

22. The method of claim 18 wherein the reservoir volume is larger than the sample volume.

23. The method of claim 17 wherein the reference medium and the reservoir medium are selected from the group consisting of liquids, gels and solids, with or without buffers or complexing agents.

24. The method of claim 23 wherein the reference medium is a gel.

25. The method of claim 17 wherein the reference medium and the reservoir medium contain liquid solvents for the species of interest.

26. The method of claim 17 further comprising the step of controlling the concentration of a plurality of gaseous species of interest.

27. The method of claim 17 wherein the reservoir volume is larger than the sample volume.

28. The method of claim 17 wherein the species of interest is carbon dioxide ($CO_2$).

29. The method of claim 28 wherein the reservoir medium is an aqueous medium buffered to a $pH \geq 8.0$ and the sample medium is an aqueous medium with a $pH \leq 7.7$.

30. A packaged multi-phase reference system containing controlled amounts of at least one gaseous species of interest comprising:

a reference medium containing known reference concentrations of each gaseous species of interest;

a gas-permeable reference enclosure containing the reference medium containing the gaseous species of interest;

a separate gas permeable source of greater sensitivity to temperature change over a selected range of the gaseous species of interest comprising a reservoir having a reservoir medium containing an amount of the gaseous species of interest and being in gas-permeable relation therewith;

a substantially gas-tight hollow structure in the form of a common enclosure for containing both the reference enclosure and the reservoir surrounded by a gas phase that forms a common atmosphere;

the reservoir functioning via the gas-permeable reservoir enclosure and common atmosphere to vary a partial pressure of the gaseous species of interest contacting the gas-permeable reference enclosure as a function of temperature such that the reference concentration of the gaseous species of interest in the reference medium remaining substantially constant over the selected temperature range.

* * * * *

UNITED STATES PATENT AND TRADEMARK OFFICE
CERTIFICATE OF CORRECTION

PATENT NO. : 5,223,433
DATED : June 29, 1993
INVENTOR(S) : David W. Deetz et al

It is certified that error appears in the above-identified patent and that said Letters Patent is hereby corrected as shown below:

In column 8, line 64, delete "change sin" and insert -- changes in -- .

In column 9, line 12, before "more", insert -- , -- .

In column 9, line 13, delete "int he" and insert -- in the -- .

In column 10, line 16, delete "form" and insert --from--.

In column 10, line 36, before "more," insert --,--.

Signed and Sealed this

Twenty-sixth Day of April, 1994

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO.    : 5,223,433
DATED         : June 29, 1993
INVENTOR(S)   : David W. Deetz et al It is certified that error appears in the above-indentified patent and that said Letters Patent is hereby corrected as shown below:

On page 2 of the drawings, Figure 3, the numerals beneath the heading "TEMPERATURE (K)" should read, from left to right, "300" and "290", instead of "300" and "200".

Signed and Sealed this

Seventh Day of June, 1994

Attest:

BRUCE LEHMAN

Attesting Officer           Commissioner of Patents and Trademarks